(12) United States Patent
Gustavsson et al.

(10) Patent No.: US 11,058,847 B2
(45) Date of Patent: *Jul. 13, 2021

(54) CATHETER ASSEMBLY AND A METHOD AND SYSTEM FOR PRODUCING SUCH AN ASSEMBLY

(71) Applicant: DENTSPLY IH AB, Mölndal (SE)

(72) Inventors: Evelina Gustavsson, Osjersjo (SE); Jan Utas, Kungsbacka (SE)

(73) Assignee: DENTSPLY IH AB, Mölndal (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/353,221

(22) Filed: Mar. 14, 2019

(65) Prior Publication Data

US 2019/0201659 A1 Jul. 4, 2019

Related U.S. Application Data

(63) Continuation of application No. 14/471,044, filed on Aug. 28, 2014, now Pat. No. 10,238,832, which is a (Continued)

(30) Foreign Application Priority Data

Dec. 22, 2010 (EP) .................................. 10196593

(51) Int. Cl.
*A61M 27/00* (2006.01)
*A61M 25/00* (2006.01)
(Continued)

(52) U.S. Cl.
CPC ............ *A61M 25/002* (2013.01); *B65B 53/02* (2013.01); *A61M 25/0017* (2013.01); *A61M 25/0111* (2013.01)

(58) Field of Classification Search
CPC ............ A61M 25/002; A61M 25/0017; A61M 25/0111; B65B 53/02
(Continued)

(56) References Cited

U.S. PATENT DOCUMENTS 3,967,728 A * 7/1976 Gordon ............... A61M 25/002
206/364
5,765,682 A 6/1998 Bley et al.
(Continued)

FOREIGN PATENT DOCUMENTS

EP 0217771 A1 4/1987
EP 1023882 A1 8/2000
(Continued)

OTHER PUBLICATIONS

European Search Report; Application No. 10196593.7-1526, Published Aug. 4, 2011.
(Continued)

*Primary Examiner* — Andrew J Mensh
(74) *Attorney, Agent, or Firm* — Perkins Coie LLP

(57) ABSTRACT

A catheter assembly is disclosed, comprising a catheter, such as a urinary catheter, which at least a partly is provided with hydrophilic coating. The catheter assembly further comprises a wetting fluid. The receptacle is in direct contact with the hydrophilic coating of the catheter over the part of the catheter with the hydrophilic coating. This may, for example, be achieved by using a shrink wrap material. In order to accomplish adequate wetting, channels or the like may be provided on the inner surface of the receptacle or the outer surface of the catheter.

12 Claims, 6 Drawing Sheets

Related U.S. Application Data continuation of application No. 13/331,485, filed on Dec. 20, 2011, now abandoned.

(60) Provisional application No. 61/426,052, filed on Dec. 22, 2010.

(51) Int. Cl.
  B65B 53/02 (2006.01)
  A61M 25/01 (2006.01)

(58) Field of Classification Search
  USPC .......................................................... 604/544
  See application file for complete search history.

(56) References Cited

U.S. PATENT DOCUMENTS

| | | | |
|---|---|---|---|
| 2004/0074794 A1 | 4/2004 | Conway et al. | |
| 2004/0256264 A1* | 12/2004 | Israelsson | A61M 25/002 |
| | | | 206/364 |
| 2005/0109648 A1 | 5/2005 | Kerzman et al. | |
| 2005/0143625 A1 | 6/2005 | Whitmore et al. | |
| 2008/0091145 A1 | 4/2008 | House | |
| 2009/0131917 A1* | 5/2009 | Kavanagh | A61M 25/002 |
| | | | 604/544 |
| 2016/0129219 A1 | 5/2016 | Gustavsson et al. | |

FOREIGN PATENT DOCUMENTS

| | | |
|---|---|---|
| EP | 2106821 A1 | 10/2009 |
| GB | 1465544 A | 2/1977 |
| JP | 2009523511 A | 6/2009 |
| JP | 2009279454 A | 12/2009 |
| WO | 03092779 A1 | 11/2003 |
| WO | 2006092150 A1 | 9/2006 |
| WO | 2007082540 A1 | 7/2007 |

OTHER PUBLICATIONS

Office Action for Korean Patent Application No. 10-2013-7015390, dated Oct. 26, 2018, with translation (16 pages).

* cited by examiner

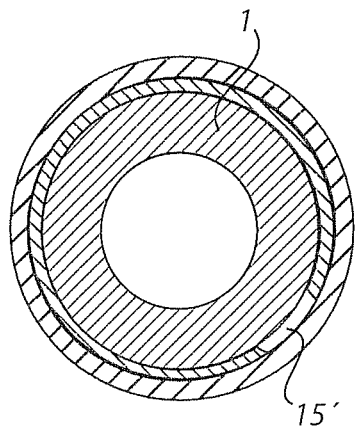
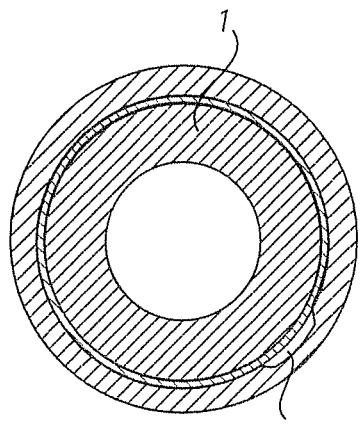
Fig. 3A    Fig. 4A
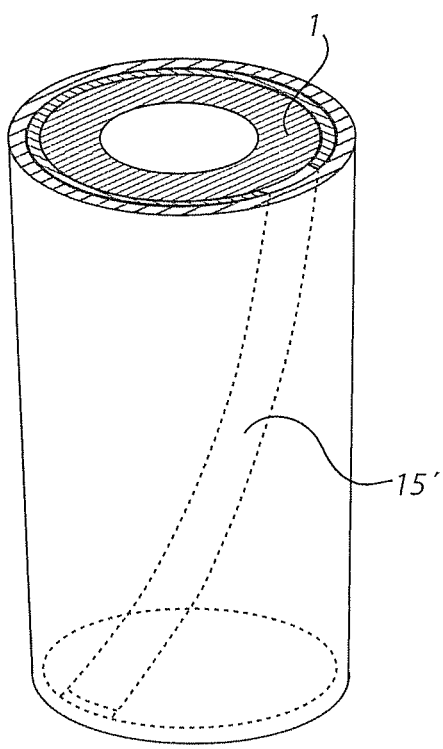
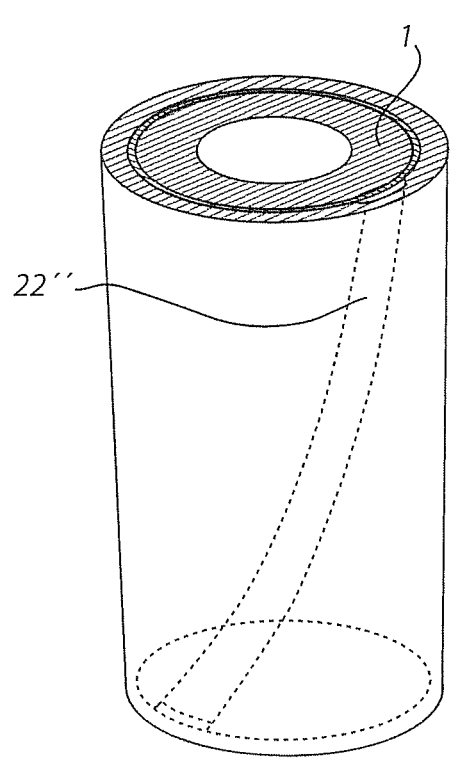
Fig. 3B    Fig. 4B

CATHETER ASSEMBLY AND A METHOD AND SYSTEM FOR PRODUCING SUCH AN ASSEMBLY

CROSS-REFERENCE TO RELATED APPLICATION(S)

This application is a continuation of U.S. patent application Ser. No. 14/471,044, filed Aug. 28, 2014, and entitled "Catheter Assembly And A Method And System For Producing Such An Assembly", which is a continuation of U.S. patent application Ser. No. 13/331,485, filed Dec. 20, 2011 and entitled "Catheter Assembly And A Method And System For Producing Such An Assembly", which claims the benefit of U.S. Provisional Application No. 61/426,052, filed Dec. 22, 2010 and entitled "Catheter Assembly And A Method And System For Producing Such An Assembly" and EP10196593.7, filed Dec. 22, 2010 and entitled "Catheter Assembly And A Method And System For Producing Such An Assembly", all of which are incorporated herein by reference in their entireties.

TECHNICAL FIELD

The present invention relates to a hydrophilic catheter assembly including a wetting fluid, and a method and system for manufacturing such an assembly. The present invention is particularly related to hydrophilic urinary catheters.

BACKGROUND

Catheter assemblies for hydrophilic catheters, including a wetting fluid for wetting and activation of the hydrophilic catheter before use have been known for over a decade. In one type of such products the wetting fluid is initially kept separate from the hydrophilic surface, and released immediately prior to use, thereby activating the hydrophilic surface. In another type of such products, the wetting fluid is arranged in such a way that the hydrophilic surface is maintained constantly wetted, and thereby ready for immediate use.

The provision of the wetting fluid in the catheter assembly entails many advantages. For example, there is no need to find a water supply, and catheterization can constantly be performed in any location and at any time.

Further, the entire wetting process can be performed under sterile conditions, without opening of the package.

However, a drawback with such catheter assemblies is that the products are relatively large and heavy and expensive to produce. In order to ensure a proper wetting, a substantial amount of wetting fluid is required, and in most products of this type, the wetting fluid in itself forms a substantial part of the overall weight of the product Further, the provision of large volumes of wetting fluid complicates the production, e.g. requiring larger doses of radiation for sterilization, and also makes logistics more complicated and expensive.

Consequently, there has for several years been a strive to develop catheter assemblies of this type requiring more limited amounts of wetting fluid. Such attempts are e.g. disclosed in EP 1 023 882, WO 2006/092150 and EP 2 106 821. However, these products still require relatively large amounts of wetting fluid in order to ensure adequate wetting, and the proposed products are relatively complex, thereby increasing the manufacturing costs.

Further, there have been attempts to reduce the amount of wetting fluid by proposing complex wetting procedures, where a limited amount of wetting fluid is moved back and forth in order to entail a proper wetting. Such solutions are e.g. disclosed in US 2005/0109648 and US 2004/0074794. However, these methods of wetting are relatively complicated, making the wetting process tedious and difficult to perform by e.g. disabled users. Further, there is a significant risk that an inadequate wetting would occur from time to time, which would be both painful and potentially harmful for the user.

There is therefore still a need for a hydrophilic catheter assembly ensuring an adequate wetting and which is less large and heavy and/or less easier and less costly to produce and distribute.

SUMMARY

There is therefore an object of the present invention to provide a catheter assembly and a method of manufacture that at least partly overcome the above-discussed problems of the prior art.

This object is achieved by means of a catheter assembly and a method and system for manufacture according to the enclosed claims.

According to a first aspect of the invention, there is provided a catheter assembly comprising:
  a catheter, at least a part of which is provided with a hydrophilic coating;
  a wetting fluid; and
  a receptacle enclosing the wetting fluid and at least the part of the catheter being provided with the hydrophilic coating;
  wherein the receptacle is in direct contact with the hydrophilic coating of the catheter over essentially the entire length of said part of the catheter being provided with the hydrophilic coating.

The catheter assembly consequently provides a receptacle which very narrowly encloses the part of the catheter being provided with the hydrophilic coating. This results in a very lean and light product, where a very limited amount of water is sufficient to ensure an easy and highly effective wetting of the entire hydrophilic surface.

This product can also be produced at a relatively low cost. Smaller sized products and less material makes it possible to use a high speed production. Further, due to smaller size and lower amount of wetting fluid, enhanced dose ratio properties can be obtained when radiation sterilization is used. Still further, lower weight and size result in smaller primary and secondary packages, which makes the production easier and less costly, and also makes the products easier and less costly to handle and store.

By means of the present invention, the amount of wetting liquid required for appropriate wetting of the hydrophilic coating may be reduced to only slightly more than the wetting fluid contained in the hydrophilic coating when wetted. Consequently, a substantial part of the wetting fluid, and preferably essentially all the wetting fluid, is in this way used for its intended purpose, viz. to be assimilated by the hydrophilic coating.

Preferably, the direct contact between the hydrophilic coating and the receptacle occurs in a number of contact points being distributed around the circumference of the catheter, said contact points being discrete contact points or contact points being continuously connected. By contact points being continuously connected is in this context meant formation of one or several continuous lines of contact, wherein each line forms a plurality or even infinite number of contact points. Since the contact points are distributed around the circumference of the catheter, a very narrow spacing between the catheter and the receptacle is ensured. Preferably, the contact points are evenly distributed around the circumference of the catheter. Such even distribution can either be obtained by discrete contact points being arranged with essentially the same distance from each other, or by continuously connected contact points or groups of closely arranged discrete points being provided at essentially the same distance from each other.

It has surprisingly been found by the present inventor that for many types of hydrophilic coatings, the wetting fluid will distribute within the coating without the need for external passageways.

However, in order to make the distribution of the wetting fluid within the package faster and more efficient, it is preferred to arrange passageways for the wetting fluid between the hydrophilic coating and the receptacle. Preferably, at least one of the inner surface of the receptacle facing the hydrophilic coating and the outer surface of the hydrophilic coating, facing the receptacle comprises a surface texture forming channels between the receptacle and the hydrophilic coating, the areas between the channels forming areas of direct contact between the receptacle and the hydrophilic coating.

Preferably, a substantial part of the hydrophilic coating is in direct contact with the receptacle. It is also preferred that at least 20% of the area of the hydrophilic coating is in direct contact with the receptacle, and even more preferably at least 30%, and most preferably at least 50%.

The catheter assembly of any one of the preceding claims, wherein the receptacle comprises a shrink-wrap film or package. Hereby, the provision of the contact between the hydrophilic coating and the receptacle becomes very easy to obtain. Packaging can be made in a relatively large receptacle, which is subsequently shrunk to a more compact state by the provision of heat. Such a catheter assembly lends itself very well for a high speed automated manufacturing process.

In order to facilitate opening of the package, for withdrawal of the catheter before use, the receptacle is preferably provided with areas or lines of weakness for facilitating opening of the receptacle. Further, tabs for tearing may be provided to further facilitate opening. Additionally or alternatively, other opening means may be provided, such as peelable openings and the like.

In one line of embodiments, the wetting fluid is arranged separate from the hydrophilic coating, said wetting fluid being releasable for wetting of the hydrophilic coating before use. For example, the wetting fluid may be arranged in a separate compartment formed in the receptacle, or in a separate wetting fluid container arranged fully or partly within the bounds of the receptacle. The release of the wetting fluid may be accomplished by means of applying a pressure on the wetting fluid compartment. Other actions for releasing of the wetting fluid may however also be used, such as twisting, bending, pulling and the like.

In another line of embodiments, the wetting fluid is arranged in direct contact with the hydrophilic coating, maintaining the hydrophilic in a wetted state. Hereby, the receptacle forms a compartment holding both the wetting fluid and at least the part of the catheter being provided with the hydrophilic coating. The wetting fluid may be provided in an amount immediately wetting and activating the catheter. However, it is also possible to provide the wetting fluid in an amount and form which gradually wets and activates the hydrophilic coating during an initial storage period.

The wetting fluid is preferably an aqueous liquid, such as water or an aqueous solution comprising an osmolality increasing agent, such as saline. However, at least in embodiments where the hydrophilic coating is maintained in a wetted state, it is also possible to use a wetting fluid in gaseous form.

According to another aspect of the invention, there is provided a method for manufacturing a catheter assembly, comprising the steps:
  providing a hydrophilic catheter;
  providing a wetting fluid;
  arranging a receptacle around the wetting fluid and at least a part of the catheter; and
  applying heat to the receptacle, thereby making it shrink, whereby the receptacle, at least partly comes into direct contact with the catheter.

With this aspect of the invention, similar advantages as discussed above in relation to the first aspect are obtainable. Further, the specific embodiments discussed in relation to the first aspect are also combinable with this second aspect of the invention.

According to still another aspect of the invention, there is provided a system for manufacturing a catheter assembly, comprising:
  means for enclosing a wetting fluid and a hydrophilic catheter in a receptacle; and
  means for applying heat to the receptacle, thereby making it shrink, whereby the receptacle, at least partly comes into direct contact with the catheter.

With this aspect of the invention, similar advantages as discussed above in relation to the first aspect are obtainable. Further, the specific embodiments discussed in relation to the first aspect are also combinable with this second aspect of the invention.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein:

FIG. 3A shows another cross-section of an embodiment of a catheter according to the invention.

FIG. 3B shows a side-view of a cut out part of the catheter assembly of FIG. 3A.

FIG. 4A shows another cross-section of an embodiment of a catheter according to the invention.

FIG. 4B shows a side-view of a cut out part of the catheter assembly of FIG. 4A.

DETAILED DESCRIPTION

Figure 1A:
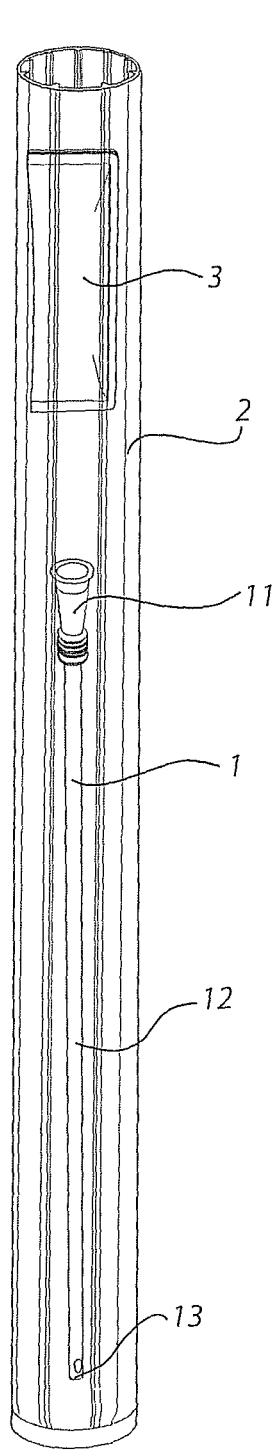
FIG. 1A is a side view showing a catheter assembly according to a first embodiment of the present invention in an intermediate production step.

In the following detailed description, preferred embodiments of the present invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, for instance the dimension of the hydrophilic coating is exaggerated. Even though in the following description, numerous specific details are set forth to provide a more thorough understanding of the present invention, it will be apparent to one skilled in the art that the present invention may be practiced without these specific details. In other instances, well known constructions or functions are not described in detail, so as not to obscure the present invention.

The catheters may be used for many different purposes, and for insertion into various types of body-cavities. However, the following discussion is in particular concerned with the preferred field of use, urinary catheters, even though the invention is not limited to this particular type of catheters.

Figure 1B:
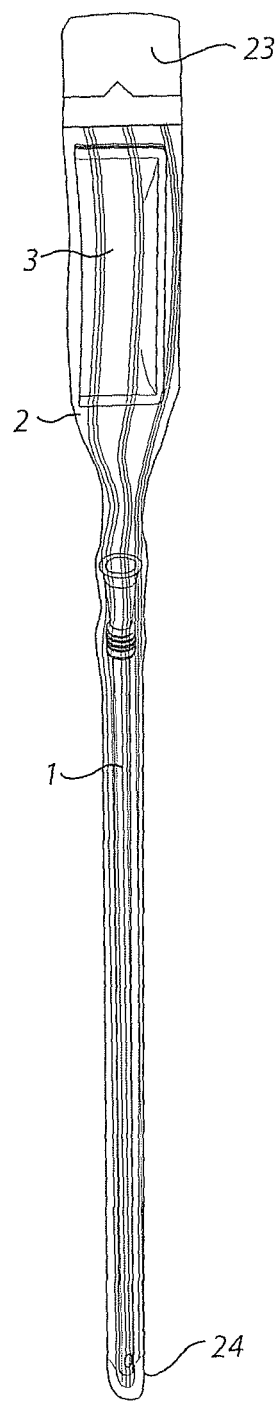
FIG. 1B is a side view showing the catheter assembly of FIG. 1A in a final configuration.

With reference to FIGS. 1A and 1B, the catheter assembly comprises a hydrophilic catheter 1, i.e. a catheter which is at least partly provided with a hydrophilic coating. The hydrophilic coating may e.g. be polyvinyl pyrrolidone (PVP), but many other types of hydrophilic coatings are known in the art, and may be used in the context of the present invention. It is also feasible to use a catheter entirely formed of a hydrophilic material, thereby making the hydrophilic coating to be an integrally formed outer surface area of said catheter. The hydrophilic coating provides a low-friction character to the catheter when wetted, thereby facilitating insertion of the catheter into the urethra, and reducing the risk of pain etc.

The hydrophilic coating is arranged on at least part of the substrate forming the catheter shaft The hydrophilic polymer coating may comprise material selected from polyvinyl compounds, polysaccharides, polyurethanes, polyacrylates or copolymers of vinyl compounds and acrylates or anhydrides, especially polyethyleneoxide, polyvinylpyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride. The preferred hydrophilic polymer is polyvinylpyrrolidone.

The hydrophilic coating preferably forms a polyurea network, whereby said polyurea network forms a covalent bond to said active hydrogen groups in the substrate. Alternatively, the hydrophilic coating may form an ester bond or an epoxy bond to said active hydrogen groups in the substrate.

The coating may also comprise an osmolality-increasing compound, as is e.g. taught in EP 0 217 771.

The elongate shaft/tube of the catheter is made of a substrate material. The substrates may be made from any polymer material, which are well-known in the technical field and to which the said hydrophilic polymers adhere, such as polyurethanes, latex rubbers, other rubbers, polyvinylchloride, other vinyl polymers, polyesters, polyether block amid, polypropene, polyethen polyamide and styrenethen/buten-styren co-polymer and polyacrylates. However, preferably the substrate is made of a polymer blend comprising a polyolefin and a composition having molecules with active hydrogen groups, and preferably a composition having molecules with active hydrogen groups. The polyolefin can comprise at least one polymer selected from the group: polyethene, polypropene, and styrene block copolymer. The composition having molecules with active hydrogen groups can be a polymer having active hydrogen groups bound to the polymer via nitrogen, such as polyamide or polyurethane.

The catheter typically comprises a flared rearward portion, i.e. a connector end 11, connected to an elongate shaft 12, wherein at least part of the elongate shaft is an insertable part, provided with said hydrophilic coating on the outer surface. The connector end may function as a connector of the catheter, being connectable to other devices, such as a urine collection bag, a drainage tube or the like. The forward end of the elongate shaft forms a rounded tip portion 13, and an internal lumen extends from the tip portion, through the elongate shaft to the connector end. However, this is only an example of a catheter to be used in the context of the present invention. Many other catheter types may be used in this context as well, such as catheters having an integrally formed funnel shaped connector end, or even without a connector. Further, the tip portion may have many different configurations, as is per se well known in the art. Further, several lumens may be provided in the catheter, and it is also feasible to use external channels instead of an internal lumen.

At least a part of the elongate tube forms an insertable length to be inserted through a body opening of the user, such as the urethra in case of a urinary catheter. By insertable length is normally, in the context of a hydrophilic catheter, meant that length of the elongate tube which is coated with a hydrophilic material, for example PVP, and which is insertable into the urethra of the patient. Typically, this will be 50-140 mm for a female patient and 200-350 mm for a male patient.

The catheter is arranged in a receptacle 2, together with a wetting fluid 3.

The wetting fluid may either be arranged in a separate container, which is openable before use of the catheter, for wetting of the hydrophilic coating or in direct contact with the hydrophilic coating. In case the wetting fluid is arranged separately from the insertable part of the catheter, the separation wall or joint could e.g. be a breakable or peelable membrane wall, but alternative embodiments are naturally feasible, such as various types of detachable or openable caps or closings. For example, the wetting fluid container may be a sachet or a pouch containing the wetting fluid, and which is openable by application of a pressure on the sachet/pouch. However, other ways of enabling opening of the wetting fluid container are feasible, such as application of a pulling force, twisting, bending, etc. Preferably the wetting fluid may be discharged without breaking or rupturing the receptacle, even though this may not be necessary, depending on the intended use, etc.

The wetting fluid is preferably an aqueous liquid, such as water or saline. Such wetting fluid containers and wetting fluids are per se well known in the art. The wetting fluid container can e.g. be made of sheet material comprising aluminum, or any other material having a moisture vapor transmission rate (MVTR) comparable to that of aluminum.

Further, the wetting fluid container may be arranged close to the distal part of the catheter (close to a first end 23 of the package), close to the proximal part of the catheter (close to a second end 24 of the package), or in any other suitable location in the assembly.

In the use situation, the user opens the wetting fluid container, preferably without opening the receptacle, so that the wetting fluid comes into contact with the hydrophilic coating. When the hydrophilic coating is adequately wetted, the catheter is removed from the receptacle and inserted into the urethra.

Figures 7, 8A, 8B:
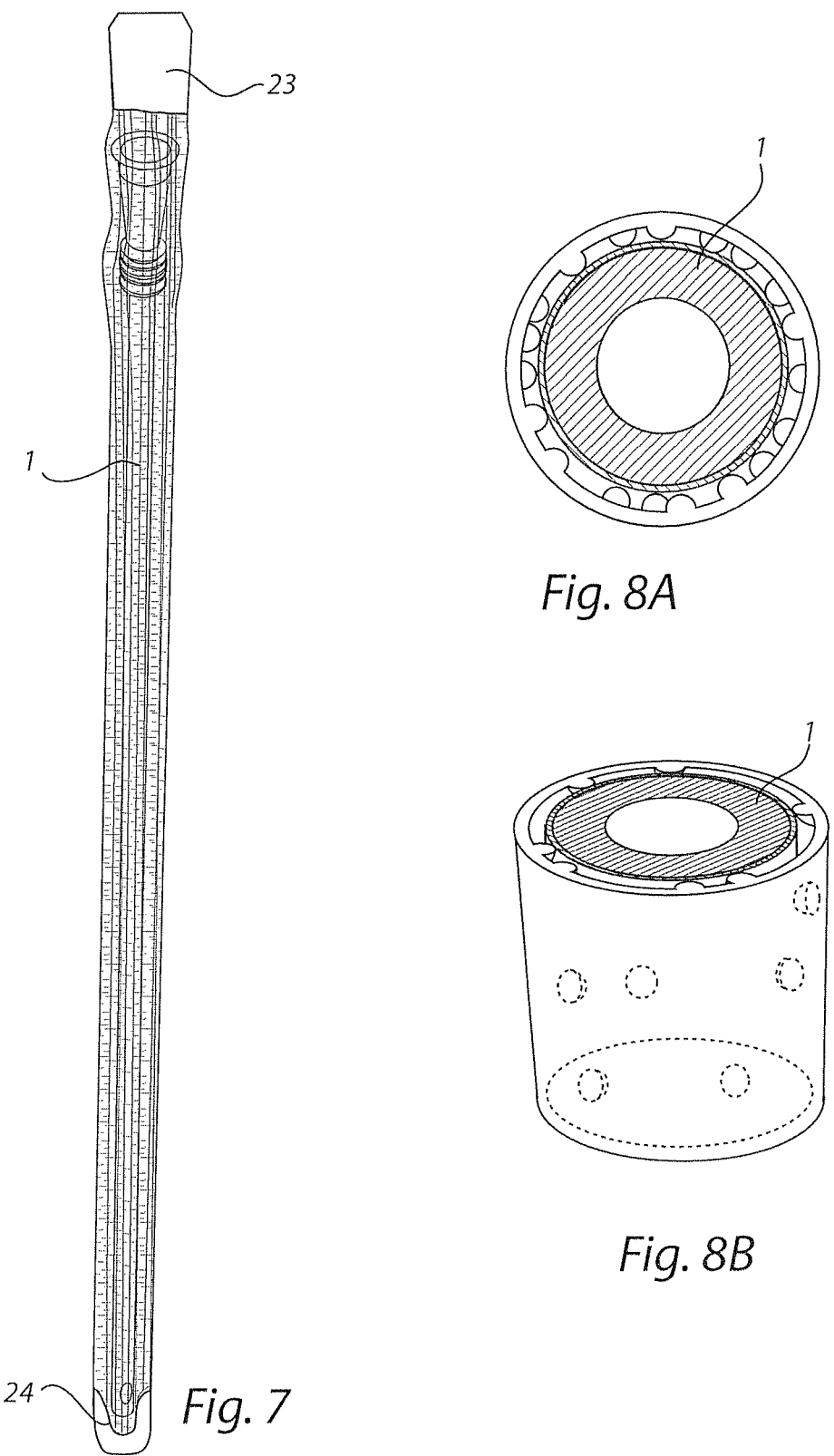
FIG. 7 shows a side view of still another embodiment of a catheter assembly according to the present invention.
FIG. 8A shows another cross-section of an embodiment of a catheter according to the invention.
FIG. 8B shows a side view of a cut out part of the catheter assembly of FIG. 8A.

It is also possible to provide the wetting fluid in direct contact with the hydrophilic coating. Such an embodiment is illustrated in FIG. 7. Hereby, the hydrophilic coating remains constantly wetted during storage, and the catheter is consequently ready for immediate use.

The wetting fluid is preferably an aqueous liquid, such as sterile water, saline or the like.

In the final configuration, the receptacle is in direct contact with the hydrophilic coating of the catheter over essentially the entire length of the part of the catheter being provided with the hydrophilic coating, as is shown in FIG. 1B. This provides a very narrow pocket housing the catheter, thereby providing a very lean product, and also significantly reducing the amount of wetting liquid required for appropriate wetting of the hydrophilic coating.

For easy manufacturing, it is preferred to use a receptacle comprising a material which is shrinkable by application of e.g. heat. Such shrink wrap packages can e.g. be made of a material comprising or consisting of polyolefin. Preferably, the material comprises at least two films, which are either crosslinked, or non crosslinked. However, other materials are also feasible, including PVC and several other compositions. The material can be of a variety of thicknesses, clarities, strengths and shrink ratios. For example, a shrink film of PVC may have a thickness in the range 75-100 gauge (0.75-1.00 mm) and a shrink film of polyolefin may have a thickness in the range 60-75 gauge (0.60-0.75 mm). Both PVC and polyolefin shrink films have excellent clarity and gloss, as well as 40% shrink factor.

Hereby, the receptacle provides a first state, in which the internal volume is relatively large, thereby enabling easy insertion of the catheter and the wetting fluid in the receptacle. This is illustrated in FIG. 1A. Thereafter, and preferably after closing the receptacle, the package is shrunk, e.g. by application of heat to the package, thereby reducing the package to the final state, as is illustrated in FIG. 18.

Depending on e.g. the type of hydrophilic coating used and the thickness of the hydrophilic coating, a wetting fluid will migrate and distribute adequately within the hydrophilic coating itself. If this is the case, it is possible to provide a receptacle which is in direct contact with the hydrophilic coating over essentially the entire hydrophilic coating. This provides the narrowest receptacle possible, and consequently enables the use of a very low amount of wetting fluid.

However, for some types of hydrophilic coating, the migration of the wetting fluid within the coating may not be sufficient to ensure proper activation of the entire hydrophilic coating, or at least such proper activation may take too long time.

To ensure adequate wetting in a limited period of time, it is preferred to provide the direct contact between the hydrophilic coating and the receptacle in a number of contact points being distributed around the circumference of the catheter, wherein the contact points are discrete contact points or contact points being continuously connected. Since the contact points are distributed around the circumference of the catheter, a very narrow spacing between the catheter and the receptacle is still ensured. Preferably, the contact points are evenly distributed around the circumference of the catheter. Such even distribution can either be obtained by discrete contact points being arranged with essentially the same distance from each other, or by continuously connected contact points or groups of closely arranged discrete points being provided at essentially the same distance from each other.

A number of embodiments illustrating such distributed contact points will now be discussed.

Figure 2A:
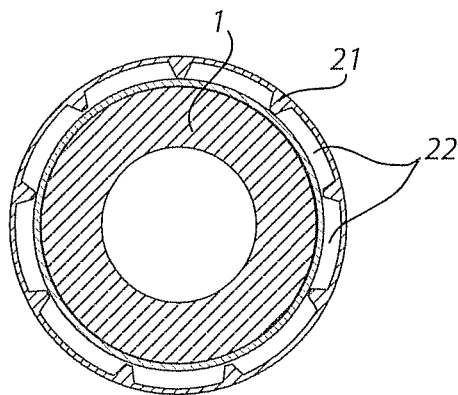
FIG. 2A shows a cross-section of one embodiment of catheter assembly according to the present invention.

According to one embodiment, as illustrated in FIG. 2A, the receptacle is provided with a number of evenly separated and inwardly facing ribs 21. These ribs forms protrusions protruding inwardly from the receptacle surface, and will consequently forming the contacts between the receptacle and the hydrophilic coating of the catheter. Between the ribs 21, channels 22 are formed, which efficiently distributes the wetting fluid over essentially the entire surface of the hydrophilic coating.

Figure 2B:
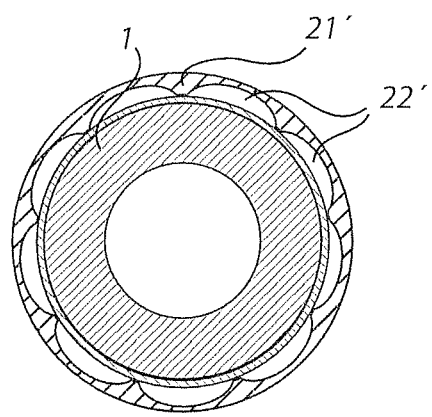
FIG. 2B shows a cross-section of another embodiment of catheter assembly according to the present invention.

Alternatively, as is illustrated in FIG. 2B, the ribs 21' may be formed by provision of smoothly rounded channels 22'.

Figure 2C:
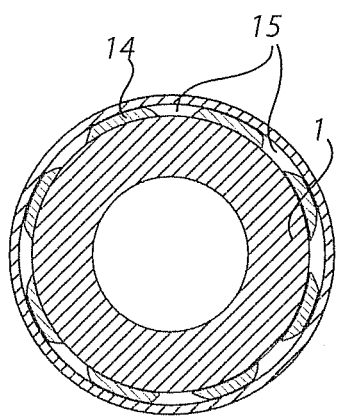
FIG. 2C shows a cross-section of another embodiment of catheter assembly according to the present invention.

Additionally or alternatively, it is also feasible to provide channels in the hydrophilic coating. Such an embodiment is illustrated in FIG. 2C, where channels 15 are formed in the hydrophilic coating 14.

Figure 2D:
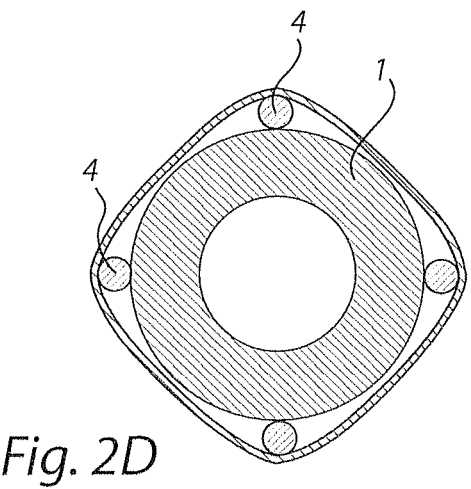
FIG. 2D shows a cross-section of another embodiment of catheter assembly according to the present invention.

Additionally or alternatively, it is also feasible to provide separate extension members 4 within the receptacle, said extension members forming a distance between the hydrophilic coating and the receptacle. Such an embodiment is illustrated in FIG. 2D. The extension members can e.g. be rods or the like of a preferably flexible material.

Instead of evenly distributed contact points, it is also feasible to provide only one or a few channels for distributing the wetting fluid in the lengthwise direction. Such a channel 15" may be formed in the hydrophilic coating, as is illustrated in FIGS. 3A and 3B. Additionally or alternatively, the channel 22" may be formed in the receptacle, as is illustrated in FIGS. 4A and 4B.

The contact points may form channels extending primarily in the lengthwise direction, as is illustrated in FIGS. 1A and 1B. Alternatively, the channels may extend helically around the catheter, as is illustrated in FIGS. 3B and 4B. However, other extension configurations of the channels are also feasible.

Figure 5:
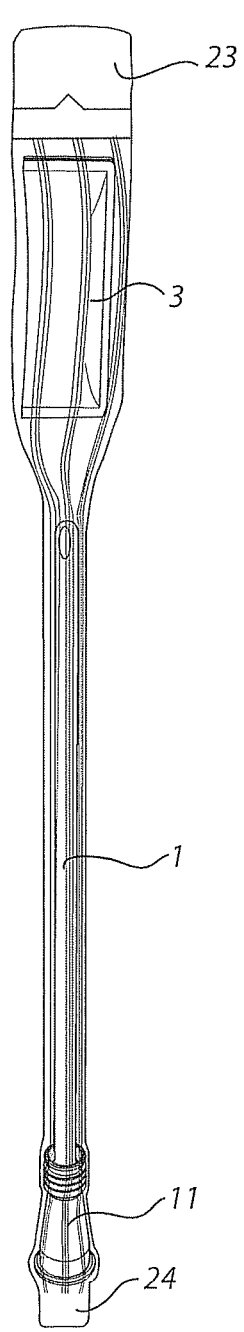
FIG. 5 shows a side view of another embodiment of a catheter assembly according to the invention.

In the embodiment illustrated in FIG. 1B, the wetting fluid container is arranged above the connector end of the catheter, i.e. opposite the insertion end. However, it is also possible to arrange the wetting fluid container above the insertion end, i.e. opposite the connector end. Such an embodiment is illustrated in FIG. 5.

Further, in order to reduce the amount of wetting fluid necessary to adequately wet the hydrophilic coating of the catheter, it is not necessary to make the entire receptacle narrow. The same effect is achievable as long as the part of the receptacle housing the insertable part of the catheter is made sufficiently narrow. Consequently, other parts of the receptacle may be still be relatively large. For example, it is possible to provide a receptacle having an enlarged portion housing the wetting fluid container. Such an enlarged part of the receptacle may e.g. be use for collecting the drained urine, i.e. forming a urine collection bag. Such an embodiment is illustrated in FIG. 6.

Figure 6:
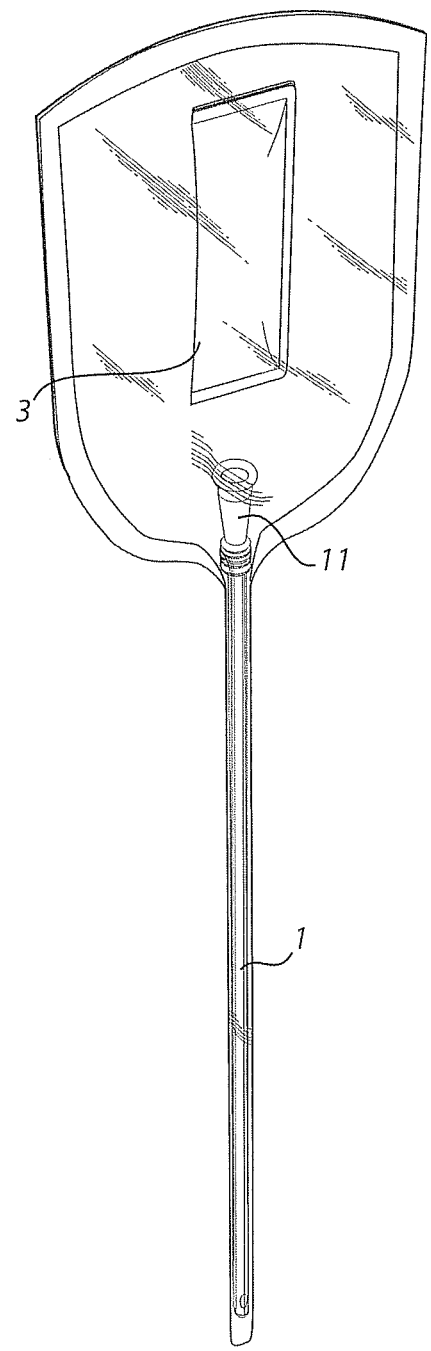
FIG. 6 shows a side view of another embodiment of a catheter assembly according to the invention.

Production of the catheter assembly illustrated in FIG. 6 is still relatively simple. For example, only the forward part of the receptacle, i.e. the part housing the insertable part of the catheter, may be shrunk, e.g. by applying heat selectively only on this part of the receptacle. Additionally or alternatively it is possible to use a thicker material, or even a different type of material, in the different parts of the receptacle.

The contact points may be arranged as continuous lines. However, it is also possible to use contact points formed as separated lines, comprising groups of contact points. However, according to another embodiment, it is also possible to use discrete contact points being evenly distributed over internal surface of the receptacle. Such an embodiment is illustrated in FIGS. 8A and 88. Hereby, a multitude of channels, each being in contact with each other, are formed.

In order to facilitate opening of the package, for withdrawal of the catheter before use, the receptacle is preferably provided with areas or lines of weakness for facilitating opening of the receptacle. Further, tabs for tearing may be provided to further facilitate opening.

Additionally or alternatively, other opening means may be provided, such as peel able openings and the like.

In FIGS. 1B, 5, 7 and 9, peel openings are indicated in both the top and bottom end of the receptacle. However, alternatively, openings may be provided only on one of said side. The openings may also be tear openings, and if tear openings are used, the openings may also be provided at a distance from the ends.

Figure 9:
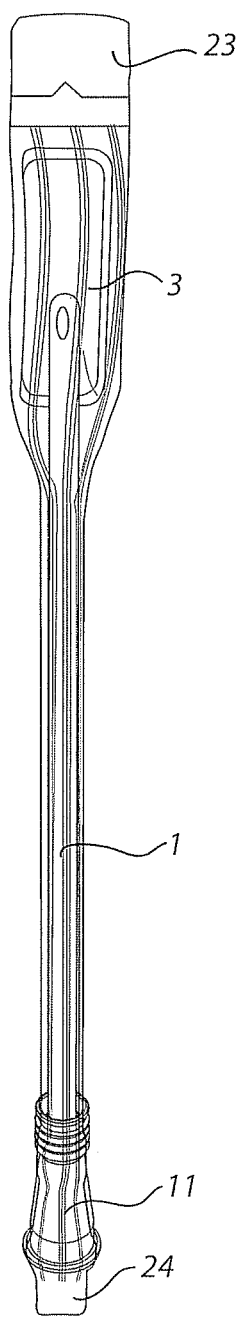
FIG. 9 shows a side view of still another embodiment of a catheter assembly according to the present invention.

In all the above-discussed embodiments having a wetting fluid container, it is also possible to provide the wetting fluid container with rounded edges, in order to reduce the strain on the receptacle. Such an embodiment is illustrated in FIG. 9. Further, it is possible to arrange the catheter with its insertion end or the discharge end (connector end) partly overlapping the wetting fluid container" Such an embodiment is also illustrated in FIG. 9.

A system for manufacturing a catheter assembly of the above-discussed type preferably comprises means for enclosing a wetting fluid and a hydrophilic catheter in a receptacle and means for applying heat to the receptacle, thereby making it shrink, whereby the receptacle, at least partly comes into direct contact with the catheter.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A catheter assembly comprising: a catheter, at least a part of which is provided with a hydrophilic coating; a wetting fluid; and a receptacle enclosing the wetting fluid and at least the part of the catheter with the hydrophilic coating; wherein the receptacle is in direct contact with the hydrophilic coating of the catheter over essentially an entire length of said part of the catheter with the hydrophilic coating, and wherein at least 20% of an area of the hydrophilic coating is in direct contact with the receptacle.

2. The catheter assembly of claim 1, wherein the direct contact between the hydrophilic coating and the receptacle occurs in a plurality of contact points distributed around a circumference of the catheter, said contact points being discrete contact points or contact points being continuously connected.

3. The catheter assembly of claim 2, wherein the contact points are evenly distributed around the circumference of the catheter.

4. The catheter assembly of claim 1, wherein at least one of an inner surface of the receptacle facing the hydrophilic coating and an outer surface of the hydrophilic coating facing the receptacle comprises a surface texture forming channels between the receptacle and the hydrophilic coating, wherein areas between the channels form areas of direct contact between the receptacle and the hydrophilic coating.

5. The catheter assembly of claim 1, wherein a substantial part of the hydrophilic coating is in direct contact with the receptacle.

6. The catheter assembly of claim 1, wherein at least 30% of the area of the hydrophilic coating is in direct contact with the receptacle.

7. The catheter assembly of claim 1, wherein at least 50% of the area of the hydrophilic coating is in direct contact with the receptacle.

8. The catheter assembly of claim 1, wherein the receptacle comprises a shrink-wrap film or package.

9. The catheter assembly of claim 1, wherein the receptacle includes areas or lines of weakness for facilitating opening of the receptacle.

10. The catheter assembly of claim 1, wherein the wetting fluid is arranged separate from the hydrophilic coating, said wetting fluid being releasable for wetting of the hydrophilic coating before use.

11. The catheter assembly of claim 1, wherein the wetting fluid is arranged in direct contact with the hydrophilic coating to maintain the hydrophilic coating in a wetted state.

12. The catheter assembly of claim 1, wherein the catheter is a urinary catheter.

* * * * *